US00PP31659P2

(12) United States Plant Patent
Jarantoski

(10) Patent No.: US PP31,659 P2
(45) Date of Patent: Apr. 14, 2020

(54) ***VITEX* PLANT NAMED 'DAVID SEARLE'**

(50) Latin Name: *Vitex hybrida*
Varietal Denomination: DAVID SEARLE

(71) Applicant: Kris Jarantoski, Glencoe, IL (US)

(72) Inventor: Kris Jarantoski, Glencoe, IL (US)

(73) Assignee: Plants Nouveau llc, Mobile, AL (US)

( * ) Notice: Subject to any disclaimer, the term of this patent is extended or adjusted under 35 U.S.C. 154(b) by 0 days.

(21) Appl. No.: 16/501,082

(22) Filed: Feb. 19, 2019

(51) Int. Cl.
*A01H 5/00* (2018.01)
*A01H 6/00* (2018.01)

(52) U.S. Cl.
USPC ..... Plt./226
CPC ..... *A01H 6/00* (2018.05)

(58) Field of Classification Search
USPC ..... Plt./226
CPC ..... A01H 5/00
See application file for complete search history.

*Primary Examiner* — Kent L Bell
(74) *Attorney, Agent, or Firm* — Cassandra Bright

(57) ABSTRACT

A new and distinct *Vitex* hybrid cultivar named 'DAVID SEARLE' is disclosed, characterized by sterile flowers on compact, shrubby plants. Foliage is uniquely rounded. Flowers are large and held on dark peduncles. The new variety is a *Vitex* hybrid, typically used for ornamental outdoor purposes.

3 Drawing Sheets

Latin name of the genus and species: *Vitex hybrida.*
Variety denomination: 'DAVID SEARLE'.

BACKGROUND OF THE INVENTION

The new cultivar was discovered as part of a planned breeding program directed by the inventor, Kris Jarantoski. The parent varieties are unidentified, as the variety resulted from an open pollination and mass collected seed from breeding blocks including several varieties of *Vitex hybrida* plants. The seed parent is and unnamed, unpatented variety of *Vitex agnus-castus*. The pollen parent is an unnamed, unpatented variety of *Vitex rotundifolia*. This crossing was made during Summer of 1994. The new variety was selected September of 1995 at a botanic garden in Glencoe, Ill.

Asexual reproduction of the new cultivar 'DAVID SEARLE' by semi-softwood vegetative cuttings was first performed in July of 1998 at a research nursery in Glencoe, Ill. The inventor has confidentially reviewed plant performance over several years. Subsequent propagation has shown that the unique features of this cultivar are stable and reproduced true to type in successive generations. Date of first sale was Jul. 1, 2018, in the United States. This sale was made directly by the inventor or one who obtained the claimed invention directly or indirectly from the inventor. This sale and all public disclosures made before the filing of this application fall within the exception allowed under 102(b)(1).

SUMMARY OF THE INVENTION

The cultivar has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DAVID SEARLE'. These characteristics in combination distinguish 'DAVID SEARLE' as a new and distinct *Vitex* cultivar:

1. Sterile flowers.
2. Uniquely rounded foliage.
3. Large flowers.
4. Compact, shrubby plant habit.

PARENT COMPARISON

Plants of the new cultivar 'DAVID SEARLE' are similar to plants of the seed parent in most horticultural characteristics. However, plants of the new cultivar 'DAVID SEARLE' differ in the following characteristics;

1. Plants of the new variety are more compact and shrubby, with denser branching.
2. The new variety produces lateral branches with maturity, producing an outwardly spreading plant. This comparator produces branches at the top of the plant, spreading upwardly.
3. Flowers of the new variety are sterile, flowers of this comparator are fertile.

Plants of the new cultivar 'DAVID SEARLE' are similar to plants of the pollen parent in most horticultural characteristics. However, plants of the new cultivar 'DAVID SEARLE' differ in the following characteristics;

1. Plants of the new variety are compact without the runner habit of the pollen parent.
2. The new variety produces lateral branches with maturity, producing an outwardly spreading plant. This comparator produces branches at the top of the plant, spreading upwardly.
3. Flowers of the new variety are sterile, flowers of this comparator are fertile.
4. Terminal inflorescence of the new variety are longer than those of the pollen parent.

COMMERCIAL COMPARISON

Plants of the new cultivar 'DAVID SEARLE' are similar to plants of the commercial variety *Vitex agnus-castus*

'Fletcher Pink', unpatented, in most horticultural characteristics. However, plants of the new cultivar 'DAVID SEARLE' differ in the following characteristics;

1. The new variety produces lateral branches with maturity, producing an outwardly spreading plant. This comparator produces branches at the top of the plant, spreading upwardly.
2. Flowers of the new variety are sterile, flowers of this comparator are fertile.
3. Flowers of the new variety are violet colored, flowers of this comparator are rose-violet colored.

Plants of the new cultivar 'DAVID SEARLE' are also similar to plants of the commercial variety *Vitex agnus-castus* 'Le Compte', unpatented, in most horticultural characteristics. However, plants of the new cultivar 'DAVID SEARLE' differ in the following characteristics;

1. The new variety produces lateral branches with maturity, producing an outwardly spreading plant. 'Le Compte' produces branches at the top of the plant, spreading upwardly.
2. Flowers of the new variety are sterile, flowers of 'Le Compte' are fertile.
3. Flowers of the new variety are violet colored, flowers of 'Le Compte' are rose-violet colored.

Plants of the new cultivar 'DAVID SEARLE' are also similar to plants of the commercial variety *Vitex hybrida* 'Helen Froehlich', U.S. Plant patent application Ser. No. 16/501,081 filed concurrently, in most horticultural characteristics. However, plants of the new cultivar 'DAVID SEARLE' differ in the following characteristics;

1. The new variety produces rounder foliage than 'Helen Froehlich'.
2. Inflorescences of the new variety are shorter than those of 'Helen Froehlich'.
3. Plants of the new variety are approximately 20% smaller at maturity in both height and width.

BRIEF DESCRIPTION OF THE PHOTOGRAPHS

The accompanying photograph in FIG. 1 illustrates in full color typical plants of 'DAVID SEARLE' grown outdoors in a trial field in Glencoe, Ill. The plants shown are approximately 4 years old.

DETAILED BOTANICAL DESCRIPTION

Figure 1:
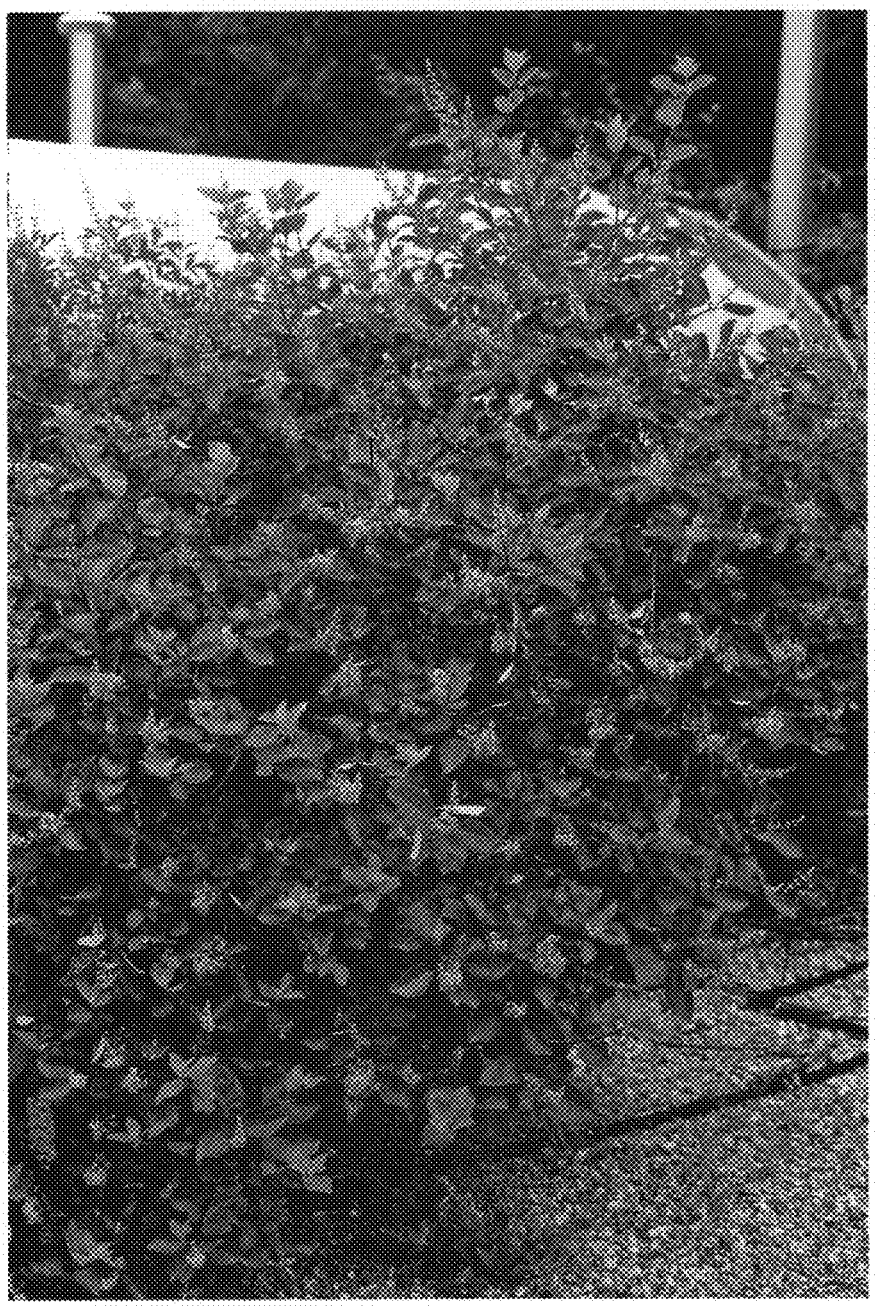
Figure 2:
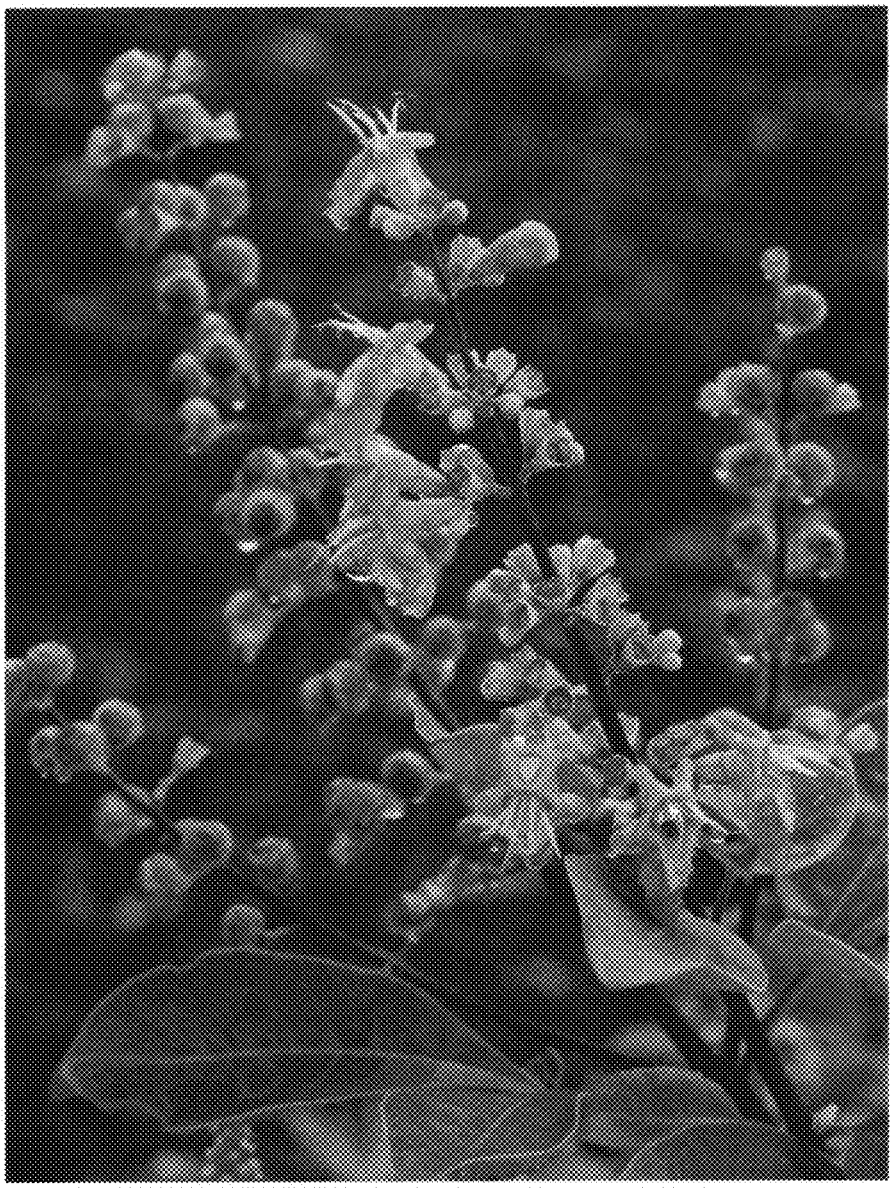
FIG. 2 illustrates a close up view of the inflorescence.
Figure 3:
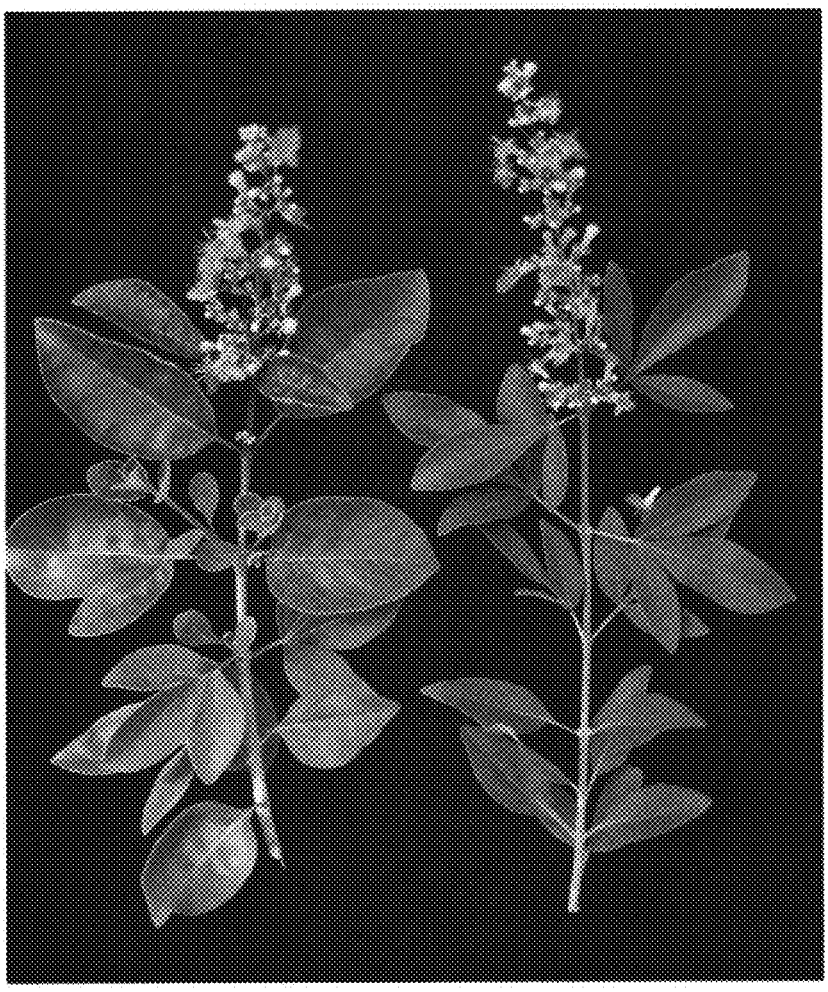
FIG. 3 illustrates inflorescence and foliage of the new variety on the left, and an inflorescence and foliage of the comparator 'Helen Froehlich' on the right. The photographs were taken using conventional techniques and although colors may appear different from actual colors due to light reflectance it is as accurate as possible by conventional photographic techniques.

In the following description, color references are made to The Royal Horticultural Society Colour Chart, 2007 except where general terms of ordinary dictionary significance are used. The following observations and measurements describe 'DAVID SEARLE' plants grown outdoors in Southern California. Measurements and numerical values represent averages of typical flowering types.

Botanical classification: *Vitex hybrida* 'DAVID SEARLE'.

PROPAGATION

Time to rooting: Approximately 20 days at approximately 20° C.

Root description: Dense, free branching, thin, fibrous. Colored tan, not accurately measured with an RHS chart.

Plant description:

Age of plant described: About 2 years in a 7 gallon container.

Growth habit: Perennial shrub. Outwardly branched, rounded.

Height: 60 cm in a 7 gallon container.

Width: 120 cm in a 7 gallon container.

Growth rate: Moderate to rapid.

Typical commercial container sizes: 3 to 15 gallon.

Branches:

*Branching habit.*—Freely branching.

*Lateral branch quantity.*—4 to 6 main lateral branches.

*Lateral branch length.*—25 to 45 cm.

*Lateral branch diameter.*—5 to 9 mm.

*Branch angle.*—Most branches 45 to 75 degrees from center.

*Branch strength.*—Strong.

*Branch color.*—Near RHS Greyed-Green 198D, moderately covered in smooth striations colored near Grey 201B.

*Internode length.*—Average range 2.0 to 4.5 cm.

Foliage:

Leaves:

*Arrangement.*—Opposite.

*Length* (*excluding petiole*).—5.0 cm.

*Width.*—4.2 cm.

*Shape.*—Orbicular.

*Apex.*—Acute.

*Base.*—Round to nearly truncate.

*Margin.*—Entire.

*Texture upper surface.*—Glabrous.

*Texture lower surface.*—Glabrous.

*Color.*—Immature: Upper: Near RHS Green 137A. Lower: Near RHS Greyed-Green 190A. Mature: Upper: RHS Green 139A. Lower: RHS Greyed-Green 190A.

*Venation.*—Color: Upper: RHS Yellow-Green 144C. Lower: RHS Yellow-Green 145B.

Petiole:

*Length.*—1 cm.

*Width.*—2 mm.

*Texture.*—Slight pubescence.

*Color.*—Upper side: RHS Greyed-Purple N187B. Under side: RHS Yellow-Green 145B.

Inflorescence:

Description: Salverform flowers arranged in panicles.

Flowering season: Spring to Mid-Summer in Southern California.

Fragrance: None.

Number of flowers per inflorescence:

*Largest central panicles.*—Average range 30 to 60 on central.

*Lateral panicles.*—Average range 10 to 40.

Inflorescence height:

*Central panicle.*—7 to 14 cm.

*Lateral panicle.*—5 to 7 cm.

Inflorescence diameter:

*Central panicle.*—4 to 6 cm.

*Lateral panicle.*—3 to 4 cm.

Flowers:

*Flower diameter.*—1.2 cm.

*Flower length.*—1.1 cm.

*Flower throat diameter.*—4 mm.

*Flower tube diameter* (*base*).—2 mm.

*Flower tube length.*—8 mm.
*Flower angle.*—About 45 to 75°.
*Persistence.*—Self-Cleaning.

Flower bud:
*Length.*—7 mm.
*Diameter.*—4 mm.
*Shape.*—Obovate.
*Color.*—RHS Violet-Blue 92C flushed 92B.

Individual flowers: The corolla is sympetalous and typically bilabiate with 2 small, highly fused lobes forming an upper lip and 3 larger highly fused lobes forming a lower lip.

Size:
*Upper lip.*—Diameter: Approximately 5 mm. Length: Approximately 4 mm.
*Lower lip.*—Length: Approximately 8 mm. Width: Approximately 7 mm.

Petals: One upper lip and one lower lip with 4 lobes. Lips are fused at base. All surfaces, including inner and outer tube are smooth and hairless.
*Tip shape.*—Upper lip: 2 rounded lobes. Lower lip: 2 rounded lobes.

Color:
*Upper lip.*—When opening: Inner surface: Near RHS Violet N88B. Outer surface: Near RHS Violet-Blue 92A. Fully opened: Inner surface: Near RHS Violet N88B. Outer surface: Near RHS Violet-Blue 91B. Fading: Inner surface: Near RHS Violet-Blue 90C. Outer surface: Near RHS Violet-Blue 91B flushed 92A.

Color:
*Lower lip.*—When opening: Inner surface: Near RHS Violet N88A, 2 center linear streaks near Violet 85D. Outer surface: Near RHS Violet-Blue 92A. Fully opened: Inner surface: Near RHS Violet N88B, 2 center linear streaks near White N155A. Outer surface: Near RHS Violet-Blue 90C. Fading: Inner surface: Near RHS Violet-Blue 90B, center linear streaks near White N155A. Outer surface: Near RHS Violet-Blue 91B flushed 92A.

Color:
*Tube.*—When opening: Inner surface: Near RHS Violet-Blue 91B. Outer surface: Near RHS Violet N88D. Fully opened: Inner surface: Near RHS Violet 85D flushed Violet 84C. Outer surface: Near RHS Violet-Blue 91C. Fading: Inner surface: Near RHS Violet 84D. Outer surface: Near RHS Violet 84D flushed Violet 84C.

Calyx: Sepals fused into a tube, tightly held around corolla.

Sepals:
*Shape.*—5 lobes entirely fused into a tube, except 1 mm acute lobes at apex.
*Length.*—Approximately 4 mm.
*Width.*—Approximately 3 mm.
*Margin.*—Entire.
*Texture.*—Slightly velvety.
*Color.*—Near RHS Greyed-Green 189B.

Peduncle:
*Length.*—Average range 1.5 to 3 cm.
*Width.*—3 to 4 mm.
*Color.*—RHS Greyed-Purple N187B.
*Texture.*—Pubescent and ridged.
*Angle.*—Very slightly outwardly curved.
*Strength.*—Strong.

Pedicels:
*Length.*—2 to 3 mm.
*Diameter.*—1 mm.
*Texture.*—Pubescent.
*Color.*—RHS Greyed-Green 191C.
*Strength.*—Good.
*Angle.*—About 45°.

Reproductive organs:

Stamens:
*Number.*—4.
*Filament length.*—Approximately 8 mm.
*Filament color.*—Near RHS Violet 85A.

Anthers:
*Shape.*—Obovate.
*Length.*—Approximately 2 mm.
*Color.*—Near RHS Violet 86D.
*Pollen.*—Not detected.

Pistil:
*Number.*—1.
*Length.*—Approximately 1.8 cm.
*Style.*—Length: Approximately 1.6 cm. Color: Near RHS Violet 84A.
*Stigma.*—Shape: 2-parted. Color: Near RHS Violet 83A. Ovary color: Near RHS Greyed-Green 191B.

OTHER CHARACTERISTICS

Disease and insect resistance: No significant disease or pest resistance nor susceptibility have been observed.

Temperature tolerance: USDA Zones 5-9.

Fruit/seed production: Fruit and seed production have not been observed in the new cultivar.

What is claimed is:

1. A new and distinct cultivar of *Vitex* plant named 'DAVID SEARLE' as herein illustrated and described.

* * * * *